United States Patent [19]

Meyst et al.

[11] 4,170,056

[45] Oct. 9, 1979

[54] BLOOD FILTER

[75] Inventors: Richard P. Meyst, Crystal Lake; Ronald M. Porten, McHenry, both of Ill.

[73] Assignee: Baxter Travenol Laboratories, Inc., Deerfield, Ill.

[21] Appl. No.: 803,696

[22] Filed: Jun. 6, 1977

Related U.S. Application Data

[62] Division of Ser. No. 670,317, Mar. 25, 1976, abandoned.

[51] Int. Cl.² .............................................. B23P 15/16
[52] U.S. Cl. ............................ 29/163.5 F; 128/214 B; 210/446
[58] Field of Search .......................... 29/163.5 F, 469; 128/214 B, 214 C; 210/446, 435, 448, 449, 500–509, DIG. 23, 451, 452, 483, 484, 488, 490, 491, 492, 496

[56] References Cited

U.S. PATENT DOCUMENTS

| | | | |
|---|---|---|---|
| 2,341,414 | 2/1944 | Poliuka | 210/185 |
| 3,003,643 | 10/1961 | Thomas | 210/491 |
| 3,158,532 | 11/1964 | Pall et al. | 210/503 |
| 3,253,715 | 5/1966 | Painter et al. | 210/504 |
| 3,327,859 | 6/1967 | Pall | 210/266 |
| 3,593,854 | 7/1971 | Swank | 210/436 |
| 3,737,036 | 6/1973 | Kasten | 29/163.5 F X |
| 3,765,536 | 10/1973 | Rosenberg | 210/446 |
| 3,935,111 | 1/1976 | Bentley | 210/446 |

Primary Examiner—C. W. Lanham
Assistant Examiner—D. M. Gurley
Attorney, Agent, or Firm—Henry W. Collins; Garrettson Ellis; Paul C. Flattery

[57] ABSTRACT

A filter for blood and the like including a housing defining an inlet for fluids to be filtered, and an outlet for filtered fluid, plus a stack of filter pads of thermoplastic fibers positioned within the housing. According to one aspect of this invention, the stack of pads is joined together at their periphery by a heat seal to form an integral filter unit, while, typically, the stack is joined to the housing at such periphery by a second seal. In another aspect of this invention, the fluid inlet is positioned adjacent a first pad of the stack and the fluid outlet is adjacent a last pad of the stack, the diameter of the fibers of the last pad being smaller than the diameter of the fibers of the first pad, typically with the fiber diameter of intermediate pads generally decreasing from pad to pad in the direction of the last pad.

7 Claims, 4 Drawing Figures

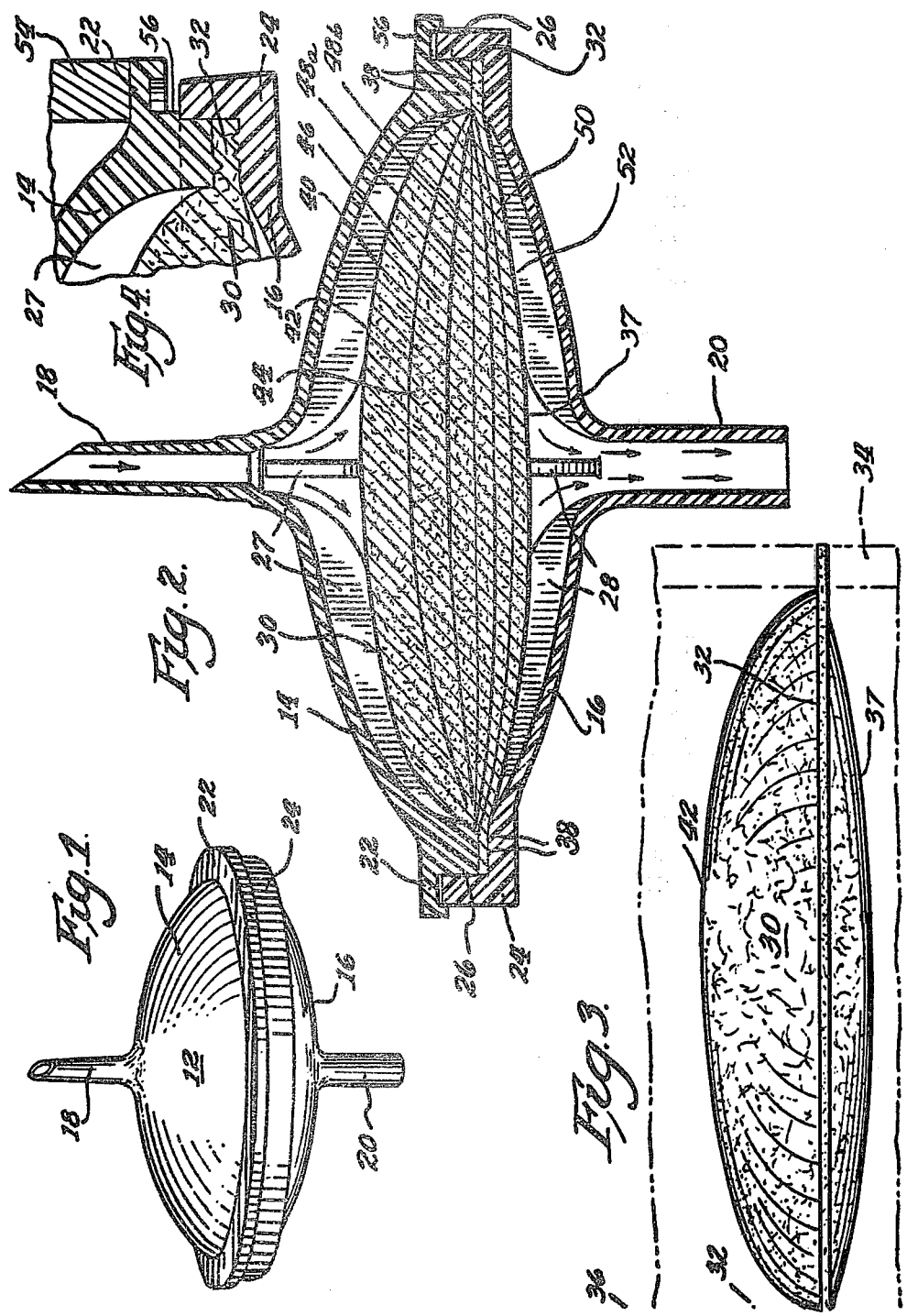

BLOOD FILTER

This is a division of application Ser. No. 670,317 filed Mar. 25, 1976 now abandoned.

BACKGROUND OF THE INVENTION

It has been recently determined that there are many situations when stored, donated blood, as well as other types of blood and blood components, should be filtered to remove microemboli of aggregated blood elements and the like, prior to administration to a patient. In paticular, older, stored blood which is nearing its expiration date has been found to be greatly improved by filtering, to prevent the microemboli from lodging in the lungs, brain, and elsewhere, thus avoiding various degrees and types of injury to the patient.

A considerable number of blood filters are now commercially available for use with stored, whole blood, or for reprocessing fresh blood in heart-lung machines, as well as blood which has passed through a cardiotomy sucker.

In a blood filter it is, of course, desirable that the filter remove as many particles as possible which are larger than red cells (which have an average size of 7 microns), while at the same time exhibiting a rapid flow rate of blood through the filter, and a high capacity to process several units of blood. Accordingly, the filter does not have to be replaced excessively often as a patient is receiving a large amount of blood.

Furthermore, a filter should be susceptible to automated commercial production techniques, so as not to be excessively expensive. It must also be reliably leak-free. Also, it must be free of shunt passages which permit blood to pass around the filter element without filtering action.

The filter of this application exhibits excellent high-flow characteristics. At the same time it provides surprisingly excellent levels of particle removal from blood. Furthermore, it is susceptible to reliable, automated sealing against blood shunting and to sterile sealing of the contents from the exterior, on a low-cost basis.

DESCRIPTION OF THE INVENTION

In accordance with one aspect of this invention, a filter for blood and the like includes a housing defining an inlet for fluids to be filtered, an outlet for filtered fluid, and a stack of fibrous filter pads, preferably thermoplastic, positioned within the housing. The stack of pads is preferably heat sealed at the peripheries of the pads to form an integral filter unit.

In the assembly on the filter, sheets of filter material are stacked to form a plurality of layers. A heat sealing device such as a sonic sealer is then applied to the stack to stamp a circular or other closed peripheral seal. The sealing operation causes the plastic pad materials to become molten, thus joining the layers to each other in the area of the seal. The sealed area then hardens to define a generally stiff and nonporous pheripheral flange for the filter stack, which can act as a sealing gasket, cooperating with the outer casing to provide a peripheral seal against the filter.

Simultaneously with the heat sealing, or thereafter, the integral filter unit is cut way about its periphery from the rest of the filter material. It is then washed and processed for installation into a housing.

In a second aspect of this invention, the inlet of the housing is positioned adjacent a first pad of a stack of pads forming an integral filter unit. The outlet to the filter is positioned adjacent a last pad of the same stack, generally on the other side from the inlet and the first pad.

The diameter of the fibers of the past pad is selected to be smaller than the diameter of the fibers of the first pad. Preferably, intermediate pads in the stack between the first and last pads have fiber diameters which are generally at least as great as the fiber diameter of the immediately adjacent pad in the direction of the last pad, with the fiber diameter generaly decreasing overall from pad to pad in the direction of the past pad. Accordingly, as microemboli pass through the filter of this invention, the large microemboli first encounter the larger-diameter fibers, and can wrap around them into adhering relationship in the manner described in the article by Swank, *New England Journal of Medicine*, Vol. 265, pp. 728–733 (1961).

The diameter of the strands can be appropriately proportioned to be of an optimum size to receive the largest of the range of expected microemboli. Thereafter, as blood passes through the stack of pads, it encounters strands of decreasing diameter, which are proportioned to promote the adhesion of smaller microemboli.

The smallest microemboli encounter the typically smallest diameter fibers of the last pad, where the adhere in a manner which is apparently similar to that described in the Swank article cited above, although applicants do not wish to be limited to any specific, theoretical mode of operation of the filter of this invention.

It is believed that the filter of this invention provides more effective adhesion of microemboli than do the typical filters of the prior art which utilize fiber strand diameters of constant size. It is believed that one specific diameter of fiber strands may be too small to efficiently retain large microemboli, while a larger strand diameter which efficiently retains large microemboli may be too large to permit the efficient adhesion of small microemboli. Accordingly, the graduation of fiber diameters utilized in the filter of this invention is believed to provide more thorough adhesion of microemboli of all sizes.

It is also preferred for the average size of the spaces between the fibers of the last pad to be less than the same average size in the first pad. This facilitates the selective filtration of larger filterable elememts from the blood in the vicinity of the first pad and the filtration of the smallest filterable elements in the vicinity of the last pad. The average size of the spaces between the fibers generally decreases from pad to pad in the direction of the last pad.

The average space size mentioned above is a function of the percentage of the total pad volume occupied by the fibers, the average space size decreasing as such percentage increases.

It has been found that nonwoven filter pads for use in the stack, and in particular filter pads made of polyester fibers, give excellent results. Polyester fibers have the advantage of being easily sonic-sealed. However, it is contemplated that other fibrous materials such as nylon, acrylic materials such as poly(methyl methacrylate), cellulose ester materials such as cellulose acetate, and polypropylene can also be used. Non-thermoplastic fibrous materials such as rayon and glass can also be utilized to construct devices in accordance with the second aspect of this invention, or in the first aspect of this invention if the nonporous peripheral flange is made by molding an adhesvive rubber or plastic ring about the periphery of the filter pads.

In the drawings;

FIG. 1 is a perspective view of one embodiment of the filter of this invention, adapted specifically for the processing of donated, stored blood.

FIG. 2 is an enlarged sectional view of the filter of this invention.

FIG. 3 is an elevation view of a stack of filter pads used in the device of FIGS. 1 and 2, being joined together at their peripheries to form an integral filter unit, prior to assembly into the filter housing as shown in FIG. 2.

FIG. 4 is a fragmentary sectional view of a portion of the structure of FIG. 2, shown prior to a heat sealing step for sealing the housing, the completion of which is as shown in FIG. 2.

Referring to the drawings, a filter is shown defining a housing 12, made of a pair of mating shells 14, 16. The filter may be connected to a blood administration set or the like for use, for receiving blood from a blood bag. Shell 14 defines an inlet 18 for fluids to be filtered, while shell 16 defines an outlet 20 for filtering fluid. Shells 14, 16 also respectively define mating flanges 22, 24, which may fit together by sonic sealing or the like at area 26. Each shell 14, 16 defines a series of radial vanes 27, 28, for the purpose of defining flow channels to distribute fluid between the filter material and inlet 18, as well as outlet 20.

Integral filter unit 30 comprises a stack of filter pads of thermoplastic fibers, positioned within housing 12 and joined together by a peripheral flange 32, which may be prepared by heat sealing, forcing the periphery of all of the pads of stack 30 into an integral, fused mass forming flange 32. This process is indicated by FIG. 3, showing how tubular heat-seal dies 34, 36 can pinch the pads together at the area of peripheral flange 32 and effect heat sealing, by means of sonic sealing, R.F. sealing, or any other desired technique, so that the stack of pads 30 form an integral mass, surrounded by fused flange 32.

Thereafter, stack 30 is inserted between shells 14, 16, and the shells are heat sealed together about flanges 22, 24 in the manner shown in FIG. 2. Gripper rings 38 molded on flanges 22, 24 in shells 14, 16 press against the flange 30 of stack 30 to provide a mechanical seal between stack 30 and shells 14, 16. This prevents the formation of shunting channels leading around stack 30. Optionally a heat seal may be provided in the same area, along with the mechanical seal.

In the specific embodiment shown, stack 30 comprises five different types of filter pads.

Filter pad 40 comprises the first pad of the stack. Typically, it is made of nonwoven, polyester fibers of the largest fiber diameter in the filter. Specifically, the fibers may be 15 denier (0.00392 centimeter in diameter), although the diameter may vary substantially depending upon the desired results for the filter. Pad 40 may typically be on the order of 1 to 1½ inches thick (specifically about 1¼ inches in thickness) prior to being sealed together into stack 30, which results in compression and reduction of the thickness.

Prior to assembly, the layer of nonwoven material from which fibrous pad 40 is manufactured may preferably be coated on both sides with a binder material such as a water emulsion of a self-crosslinking acrylic material, specificaly Rohm & Haas Rhoplex HA 12.

Approximately 2.5 ounces of binder material solids may be applied per square yard of fibrous material of pad 40. The upper surface 42 of fibrous pad 40 is sprayed with a 25 percent solids emulsion, while the bottom surface 44 of pad 40 may be sprayed with a 5 percent solids emulsion, so that about 5 times as much binder material is applied to surface 42 than to surface 44.

Thus, when the fibrous pad 40 is compressed by the sealing step of FIG. 3, and further compressed by being placed in housing 12, most of the compression takes place in the lower portion of pad 40, in the vicinity of bottom surface 44, while the fibrous material in the vicinity of surface 42 remains in less compressed condition. This provides a natural filtering gradient, selective for removing of the largest particles first as fluid passes through pad 40.

The total typical weight per square yard of the material of pad 40 after binder application is about 9 to 11 ounces, and the figers occupy about 4 percent of the pad volume.

The second filter pad 46 may comprise nonwoven polyester fibers of about 6 denier, i.e. a fiber diameter of 0.00264 cm.. Of course, other size ranges and materials for filter pad 46 can also be used in accordance with this invention.

Typically, before sealing into stack 30 as shown in FIG. 3, the uncompressed thickness of filter pad 46 is about ¾ to 1 inch, or specifically, ⅞ inch. The material may be treated with the same binder agent and in a manner similar to filter pad 40, with about one fourth of the weight of the resulting product constituting binder material. The overall weight per square yard of the material of pad 46, after application of the binder material, may be in the order of 3.5 to 4.5 ounces, specifically about 4 ounces, and the pad volume occupied by its fibers may also be about 11 percent.

The next two layers of filter pads 48a, 48b may be of the same polyester fiber. Before compression into stack 30 each layer 48a, 48b may be about 0.03 to 0.07 inch thick, specifically 0.05 inch. This material tends to compress much less upon processing and placement into housing 12 than the previous layers. It also can have a fiber denier of 6, but it may be a denser material than pad 46, weighing from about 6.5 to 8.4 ounces (e.g. 8 ounces) per square yard, with the fibers occupying about 11 percent of the pad volume. Typically, the materials of layers 48a and 48b are not treated with a binder. The specific filter pads 48a, 48b used may contain a polyester spunbonded scrim material as a support.

Filter pad 50 may typically contain a mixture of fibers, 50 percent by weight of which are from 3 to 6 denier (i.e. strand diameters of 0.00171 cm. to 0.00264 cm.), and 50 percent by weight of 1.5 denier fibers (a diameter of 0.00122 cm.). The material is typically made of polyester fibers, having an uncompressed thickness of about 0.03 to 0.05 inch (specifically 0.04 imch). It may have a density of about 6 ounces per square yard, and the fibers may occupy about 15 percent of the pad volume. The material is supported with a nonwoven rayon scrim material, and, in the specific embodiment, it is not treated with a binder material.

Finally, last pad 52 may be a polyester fiber mixture of 50 percent by weight of fibers having a denier of about 3 or 4, and 50 percent by weight of fibers having a denier of 1.5. The pad may have an uncompressed thickness of about 0.05 to 0.06 inch, and is supported on a polyester woven mesh scrim material. The density may be about 12 ounces per square yard, and the fibers occupy about 30 percent of the pad volume. No binder is typically used.

Of course, other filter pads, having different characteristics and properties may be used in this invention, the above description being purely for exemplary purposes.

The overall compressed thickness of filter stack 30, installed in casing 12, may be about ¾ to 1 inch in this embodiment, specifically ⅞ inch.

After the filter pads are sealed together into stack 30 by means of sonic sealing member 34, 36, and stack 30 is cut away from the rolls of bulk material, either simultaneously with the sealing process or later from the layers of bulk filter material, stack 30 is thoroughly washed. The washing solution may comprise one quarter percent by weight each of Dupanol RA detergent material sold by the DuPont Chemical Company, and sodium carbonate, in distilled water. This is followed by rinsing stack 30 three times in distilled water, and drying stack 30 in a tumble dryer at a temperature below the softening temperature of the softening or degradation temperature of the plastic fibers in stack 30.

After drying of pad 30, the bottom surface 37 of the pad is heat-sintered prior to placing the stack into casing 12. This tends to cause individual, free fibers and other particles to adhere to the pad, reducing the amount of particulate matter falling out of the pad during use. Generally, the heat-sintering step can be accomplished by exposing the bottom surface 37 of stack of pad 30 to hot air at a temperature of at least about 380° F., and preferably about 400° F., for a few seconds, for example five seconds.

Thereafter, stack 30 is placed into housing 12, with shells 14, 16 being brought together first as shown in FIG. 4. Shells 14, 16 may be sonically sealed together, for example by the use of a series 400 sonic sealer from the Branson Sonic Power Company of Danbury, Connecticut. Sonic sealing horn 54 presses shell 14 against flange 32 and lower shell 16. Simultaneously, the sonic sealing energy causes annular plastic ridge 56 to melt, resulting in the fusion of flanges 22 and 24 together in zone 26, as shown in FIG. 2.

For sealing of the shells 14, 16 of casing 12, the above described Branson sonic sealer can be used with the "silver" booster, at a power control of 85 percent, a weld time of about 1.5 seconds, a pressure of 30 p.s.i., and a hold time of 1 second.

For sealing of the various filter pads to form flange 32 and integral stack 30, the same machine may be used with the "green" booster, with a power control of 85 percent, a weld time of about 5 seconds, a pressure of about 50 p.s.i., and a hold time of about 6 seconds.

The horn of the sonic sealing device maybe adapted to cut stack 30 away from the rolls of layers of filter material, simultaneously with the sealing operation which forms flange 32.

Also, the horn of the sonic sealing device desirably contains a resilient plug to compress the fibers, particularly of filter pads 40 and 46, during the sealing operation. This can reduce the overal thickness of stack 30, resulting in a flatter filter having a lower blood volume.

The filter described above is generally capable of processing 5 or 10 units of blood without needing replacement, and has successfully removed about 64 percent of 12 micron particles; 94 to 95 percent of 16 micron particles; 98 to 99 percent or more of 20 to 32 micron particles; and all larger particles.

Casing 12 may be about 9 cm. in diameter. However, the filter of this invention, although small, exhibits a high flow capacity of excellent levels of particle removal, while being susceptible to automated and inexpensive manufacture.

The above has been offered for illustrative purposes only, and is not for the purpose of limiting the invention of this application, which is as described in the claims below.

That which is claimed is:

1. The method of manufacturing a filter which comprises assembling a stack of filter pads comprising thermoplastic fibers, and including a first pad defining an upstream outer surface and a last pad defining a downstream outer surface, heat sealing the peripheries of said pads in the stack together to form an integral filter unit defining an integral periphery, and thereafter inserting and sealing said filter unit into a filter housing by forming a seal between said integral filter unit and the filter housing along said integral periphery.

2. The method of claim 1 in which said downstream surface is heated prior to insertion of the stack of pads into the housing at a temperature sufficient to increase the adhesion of any loose plastic particles and fibers adjacent said downstrean surface to said stack of pads.

3. The method of claimm 2 in which said heat sealing step is effected by sonic sealing.

4. The method of claim 2 in which the filter pad defining said upstream outer surface is treated on both sides thereof with a binder material, the amount of binder material applied to the side of said first filter pad which defines the upstream outer surface being greater than the amount of binder material applied to the other side of said first filter pad, whereby the side of said filter pad defining said upstream outer surface is less compressable than the other side of said filter pad, and thereafter compressing said stack as it is sealed in the filter unit to obtain a differential density gradient across said first filter pad.

5. In the method of preparing a fiber-containing filter pad for emplacement in a filter housing including applying binder material to both sides of said filter pad to cause the fibers to adhere together, and thereafter compressing said filter pad in a filter housing, the improvement comprising, in combination: applying more binder material to one side of said filter pad than to the other side, to provide increased stiffness to said one side of the filter pad compared with the other side thereof, and inserting said filter pad into said housing with said one side facing the filter inlet of said housing, whereby, upon compression in the housing, said filter pad defines a compression gradient across its width caused by the differential amount of binder material on said one side compared with the other, with said other side of the filter pad being compressed more than said one side.

6. The method of claim 5 in which approximately 5 times as much binder is placed on said one side of the filter pad, compared with the amount of binder placed on the other side of the filter pad.

7. The method of claim 5 in which said fibercontaining filter pad is the first pad on a stack of filter pads, said fiber-containing filter pad defining an upstream outer surface of said filter stack.

* * * * *